United States Patent [19]
Herleikson et al.

[11] Patent Number: 5,381,803
[45] Date of Patent: Jan. 17, 1995

[54] QRS DETECTOR FOR DEFIBRILLATOR/MONITOR

[75] Inventors: Earl C. Herleikson, Groton, Mass.; James M. Lindauer, San Francisco, Calif.

[73] Assignee: Hewlett-Packard Corporation, Palo Alto, Calif.

[21] Appl. No.: 31,732

[22] Filed: Mar. 12, 1993

[51] Int. Cl.⁶ ............................................ A61B 5/0156
[52] U.S. Cl. ................................................. 128/708
[58] Field of Search ............... 128/702, 703, 704, 695, 128/696, 708; 607/5, 9

[56] References Cited
U.S. PATENT DOCUMENTS
5,010,887  4/1991  Thornander ........................... 607/9

Primary Examiner—William E. Kamm
Assistant Examiner—Marianne Parker
Attorney, Agent, or Firm—Brent F. Logan; Curtis G. Rose

[57] ABSTRACT

A high-accuracy QRS detector detects "activity" on the ECG waveform. Activity results from a steep slope of one sense followed shortly thereafter by a steep slope of the opposite sense. Low-pass filtering activity and multiplying by 2.5 yields a noise threshold. An activity peak which rises above this threshold may be a QRS complex. The detector waits three-fourths the average R to R interval after detecting a peak to allow for greater peaks to be detected. If none are, the peak is confirmed if it is either at least half the magnitude of the previous peak, or if it occurs at least three-fourths the average R to R interval after the last detected peak. This high-accuracy detector may be coupled with a fast QRS detector by providing it with the peak values of the previous three detections. The fast detector will detect if the slope is greater than three-fourths the average of the previous three detections, greater than the noise threshold, and more than 160 ms has elapsed since its last detection.

5 Claims, 17 Drawing Sheets

```
1   /*================////////////=========================
2
3       FILENAME: R_new20.c
4       PACKAGE:
5       FILETYPE: c source file
6       RCS:       $Header$
7       SOURCE:    $Source$
8
9       DESCRIPTION: This function takes a data file that contains ecg data
10                   sampled at 200 hz. and applies a simple Rwave algorithm.
11
12      DATA FORMAT: The raw data file is formatted as a standard 2-channel
13                   ECG data file with alternating 2-byte words.
14
15      ENVIRONMENT: HP-UX
16
17  ==================================================================*/
18
19  /* External Declarations */
20  #include <stdio.h>
21  #include <string.h>
22  #include <math.h>
23
24  main(argc,argv)
25  int argc;
26  char *argv[];
27
28  {
29      /* Variables declarations */
30
31      FILE      *rawfile;         /* raw input data file */
32      FILE      *ptfile;          /* patient output file descriptor */
33      FILE      *thfile;          /* threshold output file descriptor */
34      FILE      *anfile;          /* annotation output file descriptor */
35
36      char      rawfname[128];    /* raw input file name */
37      char      ptfname[128];     /* patient output file name */
38      char      anfname[128];     /* annotation file name */
39      char      thfname[128];     /* threshold file name */
40
41      long      i;                /* Loop counter */
42      short     nread;            /* Number of data items read by fread */
43      short     nwrite;           /* Number of data items written by fwrite */
44
45      short     *p1;              /* Loop pointer */
46      short     *p2;              /* Loop pointer */
47      short     X[16];            /* Input data points for channel one */
48      short     Y;                /* Output data of 50 mSec filter */
49      short     Z[16];            /* output of slope filter */
50      short     min1, max1 ;
51      short     min2, max2 ;
52      short     TH;               /* activity fn base threshold */
53      short     Tsens;
54      short     Tlast;
55      short     Tdetect;
56      short     S;
57      short     Dlast;
58      long      Trwave;           /* time of last rwave detect */
59      short     Drwave;           /* peak amplitude within 160 mSec of Trwave */
60      short     second;           /* one second timer */
61      short     peak[4];          /* peak amplitude in 1 sec with 3 sec history */
62      short     D[4];             /* amplitude of last 4 Rwaves */
63      short     noise ;
64      long      NOISE ;
65      long      time;
66      long      ltmp;
67      short     ave_RR;
68      short     T_RR;
69      short     in_data_buf[1];   /* File Input read buffer */
```

FIG. 15A

```c
70      short   out_data_buf[1]; /* File Output write data buffer */
71      short   tmp ;
72      short   tmp1 ;
73      short   C[8] ;     /* coef of filter */
74
75
76      /* Start of main() */
77
78      strcpy(rawfname,argv[1]);
79      strcpy(anfname,argv[2]);
80      if (argc > 3) strcpy(ptfname,argv[3]);
81      if (argc > 4) strcpy(thfname,argv[4]);
82
83      if (!((rawfile = fopen(rawfname, "r")) == NULL)) /* Open raw data file */
84        {
85
86        if (!((anfile = fopen(anfname, "w")) == NULL))    /* Open annotate file */
87          {
88          thfile = fopen(thfname, "w");    /* Open output threshold file */
89          ptfile = fopen(ptfname, "w");    /* Open output file */
90
91          for (i = 0 ; i < 16; i++) X[i] = Z[i] = 0;
92          for (i = 0 ; i < 4; i++) peak[i] = 200;
93          ave_RR = 50;
94          TH = 200 ;
95          C[0] = -32 ;
96          C[1] = -29 ;
97          C[2] = -20 ;
98          C[3] = -7 ;
99          C[4] = 7 ;
100         C[5] = 20 ;
101         C[6] = 29 ;
102         C[7] = 32 ;
103         for (i=0; i<4; i++) D[i]=80;
104
105         do                    /* Until end of file */
106           {                   /* Read 2 data words, 1 for each channel */
107           nread = fread((char *)in_data_buf, sizeof(in_data_buf[0]),
108                                                      1, rawfile);
109
110           if (feof(rawfile) != 0)    /* check for end of input file */
111             {
112             printf("End of file reached.\n");
113             exit(1);
114             }
115
116           X[0] = in_data_buf[0];        /* get next chan. 1 data point */
117           time++;
118           Tsens++;
119           Tlast++;
120           T_RR++;
121           Tdetect++;
122           second++;
123
124           for (p1 = X, p2 = C, i = ltmp = 0; i<8; i++, p1++, p2++)
125              ltmp += (*p1) * (*p2) ;
126           *Z = ltmp >> 6 ;                /* 30 mSec Rwave unity gain */
127                                           /* activity fn for Sync Discharge */
128           min1 = max1 = *Z ;
129           for (p1 = Z+1, i = 1; i<7; i++, p1++)
130              {
131              if (*p1 < min1) min1 = *p1 ;
132              if (*p1 > max1) max1 = *p1 ;
133              }
134           min2 = max2 = Z[9] ;
135           for (p1 = Z+10, i = 1; i<7; i++, p1++)
136              {
137              if (*p1 < min2) min2 = *p1 ;
138              if (*p1 > max2) max2 = *p1 ;
```

FIG. 15B

```
139                    }
140                 Y = abs(max2 - min1) - abs(max2 + min1) ;
141                 tmp = abs(max1 - min2) - abs(max1 + min2) ;
142                 if (tmp > Y) Y = tmp ;
143                 if (Y < 0) Y = 0 ;
144                 Y >>= 1 ;                       /* activity fn for HR meter */
145
146                 tmp = (NOISE >> 5) ;      /* limit input to LPF = 4*LPF */
147                 if (tmp < 100) tmp = 100;  /* or .25 mV  whichever is greater */
148                 if (Y < tmp) tmp = Y ;
149                 NOISE += 5*tmp ;
150                 NOISE -= NOISE >> 7 ;
151                 noise = NOISE >> 8 ;       /* noise = 2.5 * LPF */
152                 if (noise < 10) noise = 10 ; /* lower limit is .025mV threshold */
153
154     /* Do 1 sec peak history */
155                 if (second >= 200)
156                    {
157                    TH = 0 ;
158                    for (i=3; i>0; i--)
159                       {
160                       if (TH < peak[i]) TH = peak[i] ;
161                       peak[i]=peak[i-1] ;
162                       }
163                    if (TH < *peak) TH = *peak ;
164                    *peak = Y ;
165                    second = 0 ;
166                    }
167                 else if (*peak < Y) *peak = Y;
168                 if (TH < Y) TH = Y ;
169
170     /* Look for Detections */
171                 tmp = (3 * ave_RR) >> 2 ;
172                 if (tmp > 50) tmp = 50 ;    /* max = 250 mSec */
173                 if (tmp < 32) tmp = 32 ;    /* min = 160 mSec */
174                 if (Y<noise && Tsens>tmp && Drwave>0)
175                    {
176                    tmp = (3 * ave_RR) >> 2 ;
177                    if (tmp > 90) tmp = 90 ;      /* max = 450 mSec */
178                    if ((Tlast-Tsens)>tmp || Drwave>(Dlast>>1))
179                       {
180                       fprintf(anfile,"%d D\n",Trwave*5);
181                       for (i=3; i>0; i--) D[i]=D[i-1];
182                       D[0] = 0;
183                       Tlast = Tsens ;
184                       Dlast = Drwave ;
185                       }
186                    Drwave = 0;
187                    }
188                 if (Y > noise && Y > Drwave)
189                    {
190                    Drwave = Y ;
191                    Trwave = time - 8 ;
192                    Tsens = 0 ;
193                    }
194                 tmp = TH >> 1 ;
195                 if (tmp < noise) tmp = noise ;
196                 if (Y>tmp && T_RR>32)
197                    {
198                    if (T_RR > 120) T_RR = 120;
199                    if (T_RR < ave_RR) ave_RR = (3*ave_RR + T_RR) >> 2;
200                    else               ave_RR = (7*ave_RR + T_RR) >> 3;
201                    T_RR = 0;
202                    }
203                 S = abs(*Z) ;
204                 if (S > D[0]) D[0] = S;
205                 tmp = 0;
206                 for (i=1; i<4; i++)  tmp += D[i] ;
207                 tmp >>= 2 ;
```

FIG. 15C

```
208                if (tmp < noise) tmp = noise ;
209                if (abs(*Z) > tmp  && Tdetect > 32)
210                  {
211   /*                fprintf(anfile,"%d S\n",time*5);    */
212                   Tdetect = 0 ;
213                  }
214
215   /* output data */
216
217                out_data_buf[0] = Y ;    /* set output write buffer */
218
219                nwrite = fwrite((char *)out_data_buf, sizeof(out_data_buf[0]),
220                                 1, ptfile);
221
222                out_data_buf[0] = noise ;
223
224                fwrite((char *)out_data_buf, sizeof(out_data_buf[0]), 1, thfile);
225
226                for (i=15 ; i>0 ; i--)
227                  {
228                   X[i] = X[i-1];          /* Shift data in time */
229                   Z[i] = Z[i-1];          /* Same for Z */
230                  }
231
232             } while (feof(rawfile) == 0 );        /* end of do */
233
234           fclose(rawfile);
235           }
236         else
237           {
238            printf("Can't open annotation file.\n");
239           }
240
241         fclose(ptfile);
242         }
243       else
244         {
245          printf("Can't open %s.\n",ptfname);
246         }
247
248   }
```

FIG. 15D

QRS DETECTOR FOR DEFIBRILLATOR/MONITOR

BACKGROUND

When used as a defibrillator in a synchronized discharge application, a defibrillator/monitor must be able to detect the QRS complex and discharge within 60 milliseconds (ms). Since response to QRS detection and closing of the patient relays can take as much as 30 ms, a synchronous QRS detector must be able to detect with little delay.

When used as a patient monitor, the defibrillator/monitor must be able to accurately determine the patient's heart rate. More accuracy may be required in this application, but a greater time delay tn QRS detection is permissible.

For the foregoing reasons, there is a need for a QRS detector which is both highly accurate for determining a patient's heart rate, and has minimal delay for initiating a synchronous defibrillation discharge.

SUMMARY

The present invention is directed to a method and apparatus that satisfies this need.

A high-accuracy QRS detector detects "activity" on the ECG waveform. Activity results from a steep slope of one sense followed shortly thereafter by a steep slope of the opposite sense. A threshold is determined from the activity level. An activity peak which rises above this threshold may be a QRS complex.

The detector waits a variable time period after detecting a peak to allow for greater peaks to be detected. The time period preferably is three-fourths the average R to R interval. If no subsequent peaks are detected during the time period, the peak is confirmed if either its magnitude exceeds a certain fraction, such as one-half, of the magnitude of the previous peak, or if it occurs at least a certain fraction, such as three-fourths, of the average R to R interval after the last detected peak.

This high-accuracy detector may be coupled with a fast QRS detector by providing it with the peak values of the previous three detections. The fast detector will detect if the slope is greater than three-fourths the average of the previous three detections, greater than the noise threshold, and more than 160 ms has elapsed since its last detection.

These and other features, aspects, and advantages of the present invention will become better understood with reference to the following description and appended claims.

DESCRIPTION OF THE DRAWINGS

FIGS. 15A, 15B, 15C, and 15D show source code in C of a sample program listing which implements a method for detecting QRS events.

DESCRIPTION

Figure 1:
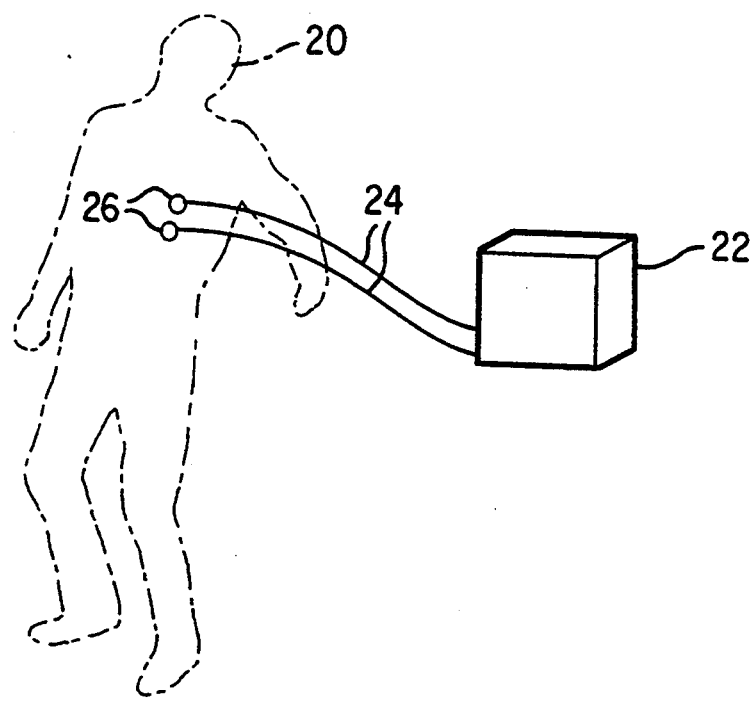
FIG. 1 shows a defibrillator and a patient.

Referring now to the drawings, a patient 20 is shown with a typical defibrillator 22 in FIG. 1. The defibrillator comprises a unit containing an electrical power source, a storage capacitor on which energy is accumulated, and switching relays for delivering the electrical energy to the patient via cables 24 and paddles 26.

Figure 2:
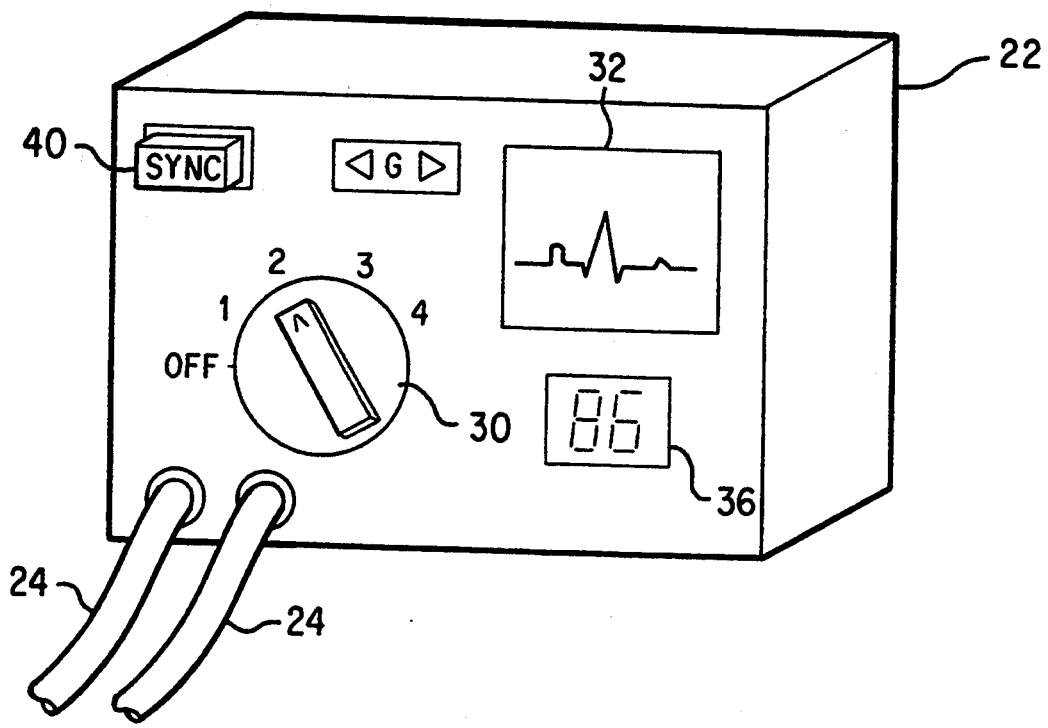
FIG. 2 shows a defibrillator.

Referring now to FIG. 2, the defibrillator 22 typically has a switch 30 for selecting the amount of energy to be delivered to the patient. The switches for initiating the discharge are typically located on the paddles 26.

The defibrillator 22 has a display 32 for showing the patient's heart waveform, enabling the operator to diagnose the patient's condition. A heart rate (HR) display 36 shows the patient's current heart rate.

One operating mode of the defibrillator is termed the "synchronous discharge" mode. In this mode, the defibrillator detects the QRS complex, and initiates discharge within 30 ms of the QRS onset. A mode switch 40 enables the defibrillator 22 to be put in synchronous discharge mode.

Figure 3:
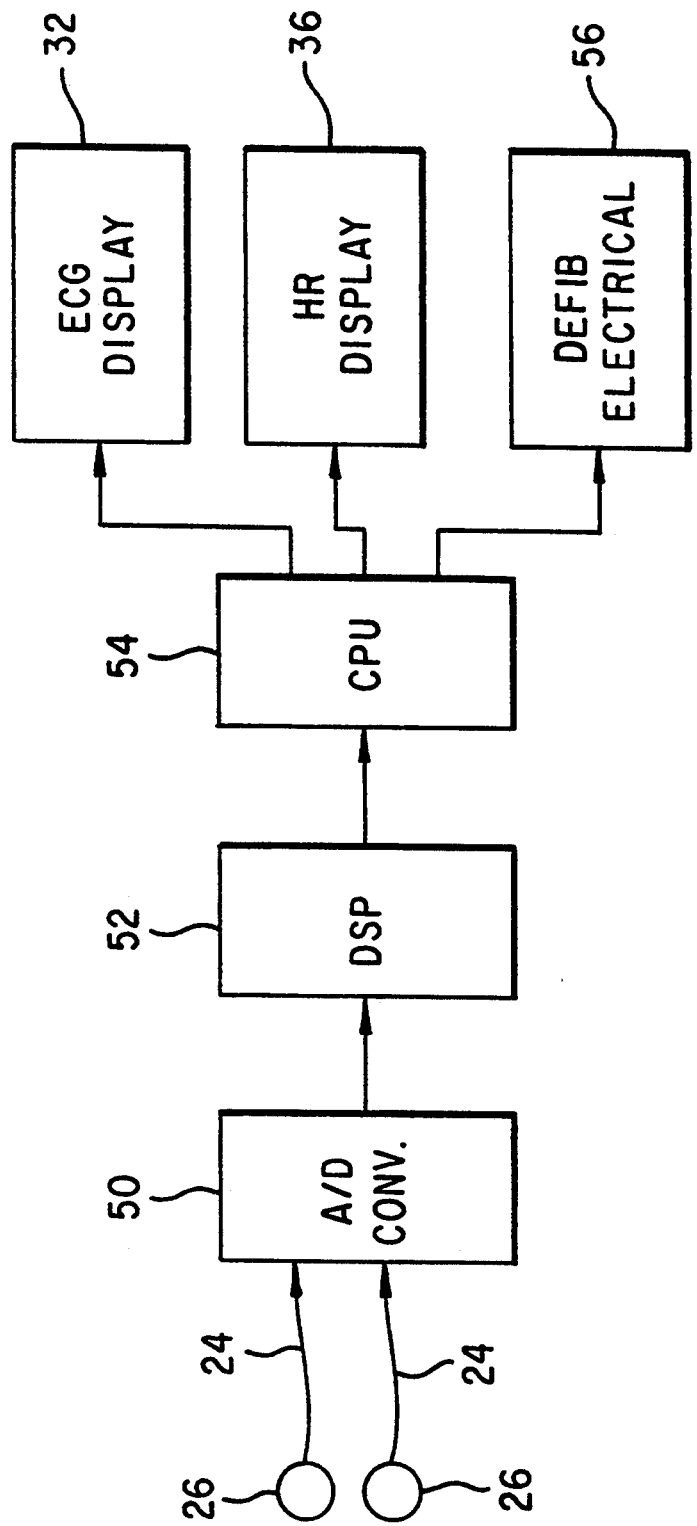
FIG. 3 shows a block diagram of an embodiment of a defibrillator.

Referring now to FIG. 3, a block diagram of the internal circuitry of the defibrillator 22 is shown. The heart waveforms are picked up by the paddles 26 and transmitted by the cables 24 to an analog-to-digital converter (A/D converter) 50. The output of the A/D converter 50 is provided to a a digital signal processor (DSP) 52 and a general purpose microprocessor (CPU) 54. The digital signal processor 52 can quickly perform filtering and detection processes on the digitized data.

The microprocessor 54 can also perform operations on the digitized data and the processed data from the digital signal processor 52, as well as control the ECG display 32, heart rate display 36, and the operation of the defibrillator electrical components 56 such as the high-voltage charger circuit and the patient relays.

A typical QRS complex can be approximated by a triangular waveform having a width of 40 to 120 ms. A QRS detector designed to effectively detect such triangular waveforms would likewise effectively detect QRS complexes. As such, a QRS detector according to the present invention detects the sloped sides of the ECG waveform, using an "activity" detector to detect when there is a steep slope of one sense followed shortly thereafter by another steep slope of the other sense. The activity detector is designed to reject waveform reversals which occur too quickly or too slowly to have resulted from actual QRS complexes.

Figure 4:
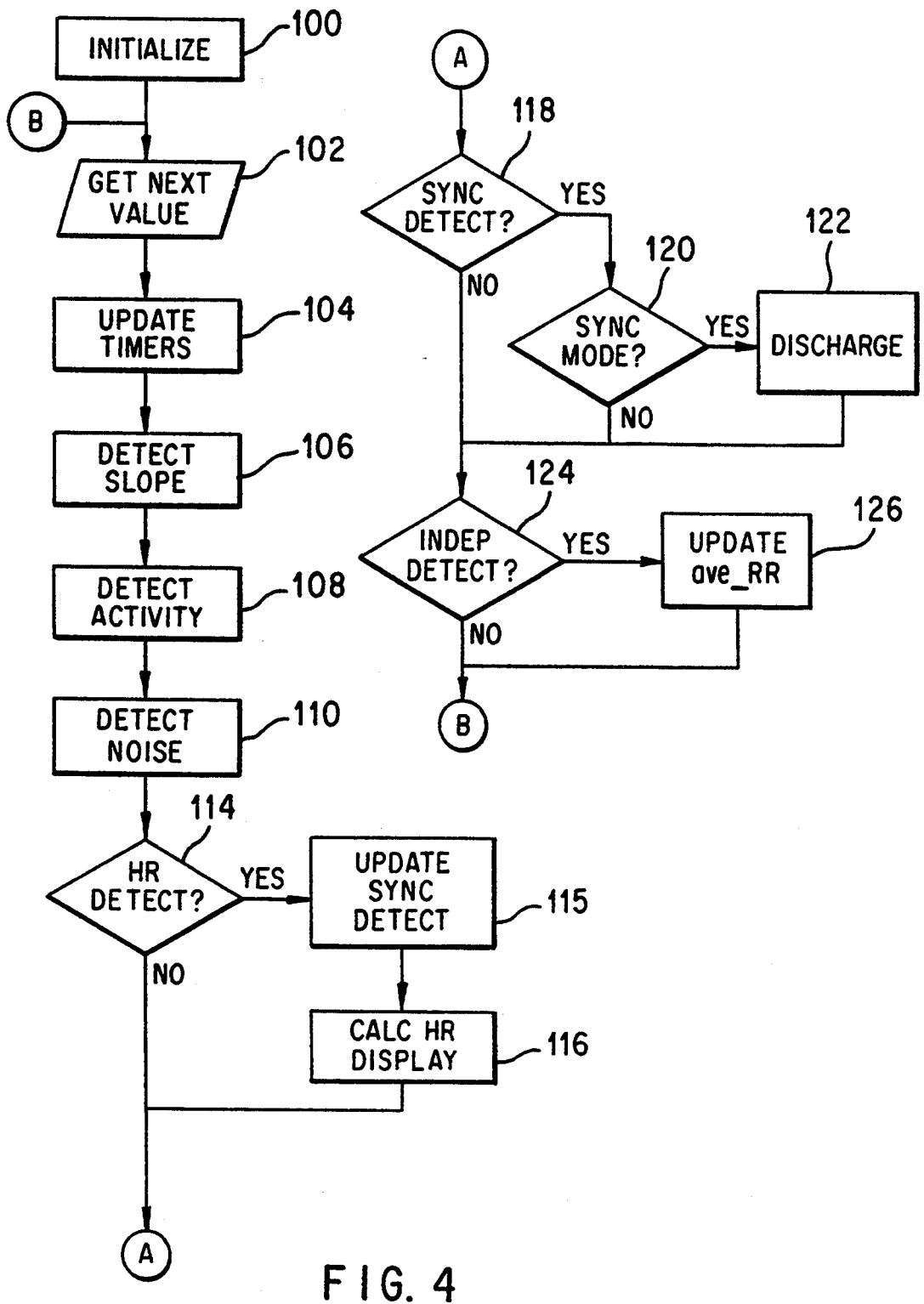
FIG. 4 shows a general flow diagram of a method for detecting QRS events.
Figure 5:
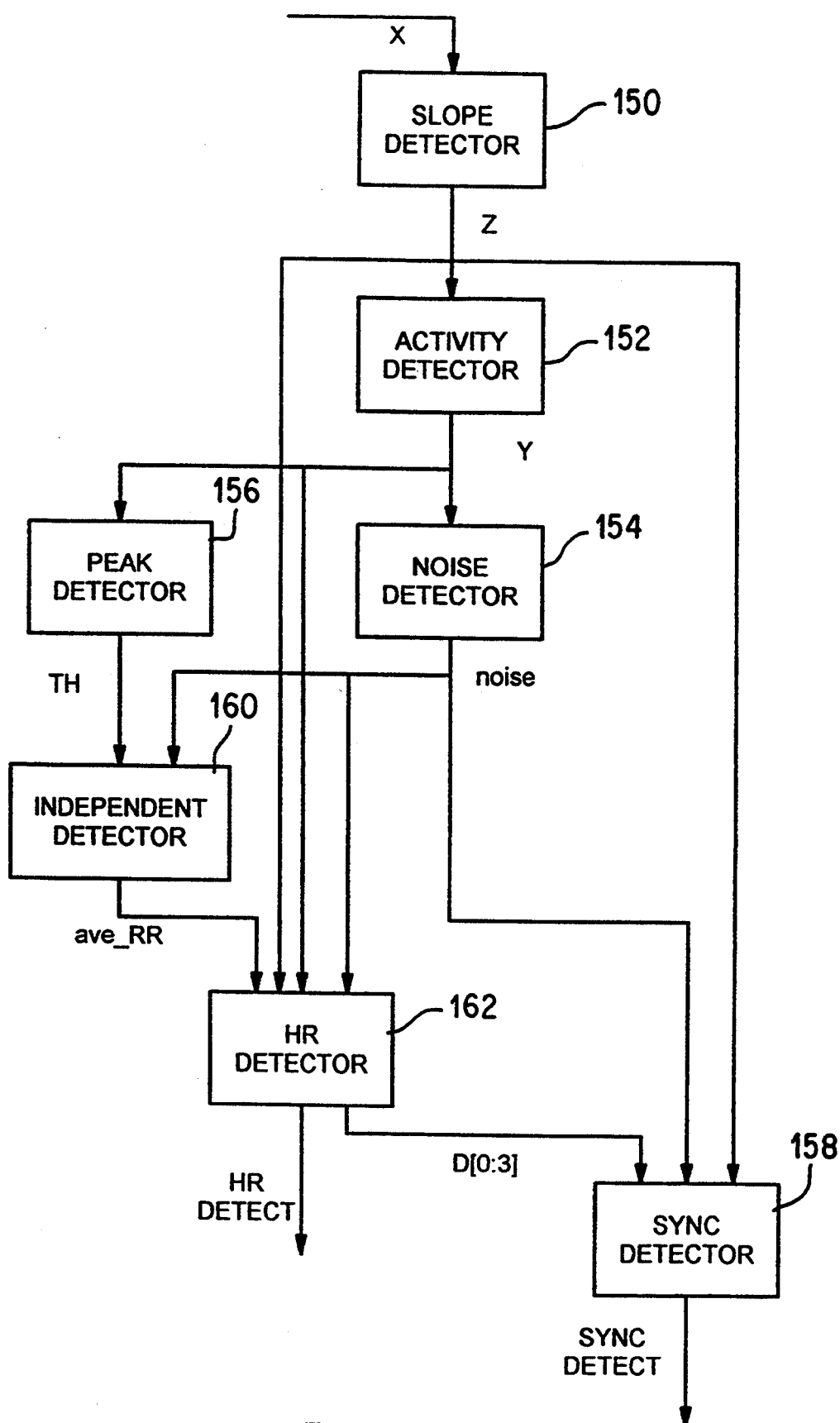
FIG. 5 shows a functional block diagram of QRS detection.

FIG. 4 shows a flow diagram of a method for detecting QRS complexes according to the present invention. FIG. 5 shows a functional block diagram of a system which can perform the method shown in FIG. 4. The following discussion will make reference to both FIGS. 4 and 5, as well as to the sample program listing given in FIGS. 15A through 15D. The individual steps shown in FIG. 4 also will be discussed in more detail in connection with other drawings.

As a first step, various timers, coefficients, and storage registers used by the detection program are initialized 100 to appropriate values. This occurs in lines 91-103 of the sample program listing.

The QRS detector processes a single channel of 16-bit ECG waveform data which is sampled at 200 samples per second, resulting in an ECG data stream of 2-byte words. As used herein, X[i] will refer to the "ith" sample in the ECG data stream X with X[0] being the most recent sample.

The main processing loop starts by getting 102 the next value of ECG data from the ECG data stream X. In the defibrillator, this next value is the most recently digitized value. The sample program shown in the listing operates on sample ECG data files. Thus, rather than reading the most recently digitized value, the program, in lines 107-116, reads the next value in the ECG data file. After reading the next value, various timers used by routines are updated 104.

A "slope detector" 150 detects 106 the "slope" Z of the input ECG data X. Actually, the slope detector is a digital filter acting as a triangular convolution filter. However, as used herein, "slope detector" will refer to a triangular convolution filter. The slope detector's coefficients are selected such that its output slope Z is the average slope of the last 40 ms of the ECG data, that is, the last eight samples. (The coefficients were initialized in block 100, above).

The formula used by the slope detector is given in equation (1).

$$Z[0] = (-32 \cdot X[-7] - 29 \cdot X[-6] - 20 \cdot X[-5] - 7 \cdot X[-4] + 7 \cdot x[-3] + 20 \cdot x[-2] + 29 \cdot x[-1] + 32 \cdot x[0])/64 \quad (1)$$

The slope detector 150 is implemented in the sample program listing in lines 124-126.

An activity detector 152 detects 108 activity Y in the ECG data stream X using a history of the last 75 ms of slope Z. Four storage registers $max_1$, $min_1$, $max_2$, and $min_2$ are used to contain the minimum and maximum values of slope in two time periods. Thus, $max_1$ contains the maximum value of slope Z from the current time to 30 ms prior, $min_1$ contains the minimum value of the slope Z during the same time period as $max_1$, $max_2$ contains the maximum value of the slope from a time period spanning 45 to 75 ms prior to the current time, and $min_2$ contains the minimum value of the slope Z during the same time period as $max_2$. Stated in another way, $max_1$ and $min_1$ contain the maximum and minimum values, respectively, of Z[i] for i in the range of $-6$ to 0. Likewise, $max_2$ and $min_2$ contain the maximum and minimum values, respectively, of Z[i] for i in the range of $-15$ to $-9$. The four values contained in $max_1$, $min_1$, $max_2$, and $min_2$ are determined in lines 128-139 of the sample program listing.

From these four values $max_1$, $min_1$, $max_2$, and $min_2$, the activity detector 152 determines the activity Y to be the largest of the following three values:

$$Y[0] = \max \text{ of} \begin{cases} 1: \dfrac{|max_2 - min_1| - |max_2 + min_1|}{2} \\ 2: \dfrac{|max_1 - min_2| - |max_1 + min_2|}{2} \\ 3: 0 \end{cases} \quad (2)$$

The first possible value for activity Y is selected when the first 70 ms of ECG data has a positive slope and the last 115 ms of ECG data has a negative slope. The second possible value for Y is selected when the first 70 ms of ECG has a negative slope and the last 115 ms of ECG data has a positive slope. Notice that one of the two conditions will be true for either a positive-going or a negative-going triangular wave 40 ms to 120 ms wide. Because of the third possible value for Y, the activity function will never have a value less than zero. The determination of activity Y is shown in lines 140-144 of the sample program listing.

The advantage of the activity detector 152 is that a single positive output of short duration will occur in response to a triangle wave input, with maximum sensitivity to triangles having widths from 40 to 50 ms. It is somewhat insensitive to T waves which are wider and contain a more gradual change from positive to negative slope. By determining the maximum and minimum values of slope Z over time, the activity detector has a broad response to all types of R waves from 20 to 120 ms, with good rejection to waves outside that width window.

A noise detector 154 low-pass filters the output Y of the activity detector 152. The low-pass filter preferably has a time constant $\tau$ of 640 ms. The noise detector multiplies the output of the low-pass filter by a factor of 2.5, yielding 110 a threshold value termed "noise." Lines 146-152 of the sample program listing perform the noise detection to result in the value noise. As will be described below, the threshold noise is used as a threshold value above which the activity Y must pass before it can be interpreted as a QRS complex.

The activity Y stays high when the input ECG data stream includes spurious high frequency signals such as could be caused by muscle artifact. In response to the increased activity, the noise detector output noise also rises above the undesired noise. However, a single narrow-width signal from a typical R wave adds little to the noise detector output noise, allowing the activity Y to rise above it and be detected.

Referring again to FIGS. 4 and 5, a HR detector 162 detects 114 the heart rate of the patient. The HR detector is a high-accuracy QRS detector, resulting in an accurate measurement of the patient's heart rate. The HR detector uses the current activity Y, the LPF output noise threshold, and the average heart rate ave_RR as determined by the independent detector 160. If the HR detector 162 detects a QRS complex 114, the sync detector 158 is updated 115 and the heart rate is calculated and displayed 116.

The HR detector will be discussed in more detail below in reference to FIG. 7.

A sync detector 158 detects 118 the QRS complex with a minimal time delay by using the slope Z from the slope detector 150, the LPF output noise, and a history D[1:3] of the magnitude of the last three QRS complexes detected by the HR detector 162. The output from the sync detector 158 can be used to initiate 122 a synchronous defibrillation discharge if 120 the defibrillator 22 is in synchronous discharge mode. The sync detector will be discussed in more detail below in reference to FIG. 8.

A peak detector 156 detects the peaks in the activity Y yielding a second threshold value TH used by the independent detector 160. The peak detector will be discussed in more detail below in reference to FIG. 6.

An independent detector 160 produces 124, 126 a value ave_RR representative of the patient's average heart rate. This value is used by the HR detector 162 in its decisions. The independent detector will be discussed in more detail below in reference to FIG. 9.

After the high-accuracy heart rate detection 114, the low-delay synchronous detection 118, and the third independent detection 124, the next value is read 102.

As discussed above, the purpose of the HR detector 162 is to provide an accurate measurement of the patient's heart rate. It is not necessary that each QRS complex be identified immediately. Rather, it is important each complex be accurately identified, with reasonable lags in detection being acceptable.

As shown in FIG. 5, the HR detector 162 uses the activity Y from the activity detector 152, the slope Z from the slope detector 150, the average heart rate ave_RR determined by the independent detector 160 (described below), and the threshold noise from the low-pass filter 154.

Figure 7:
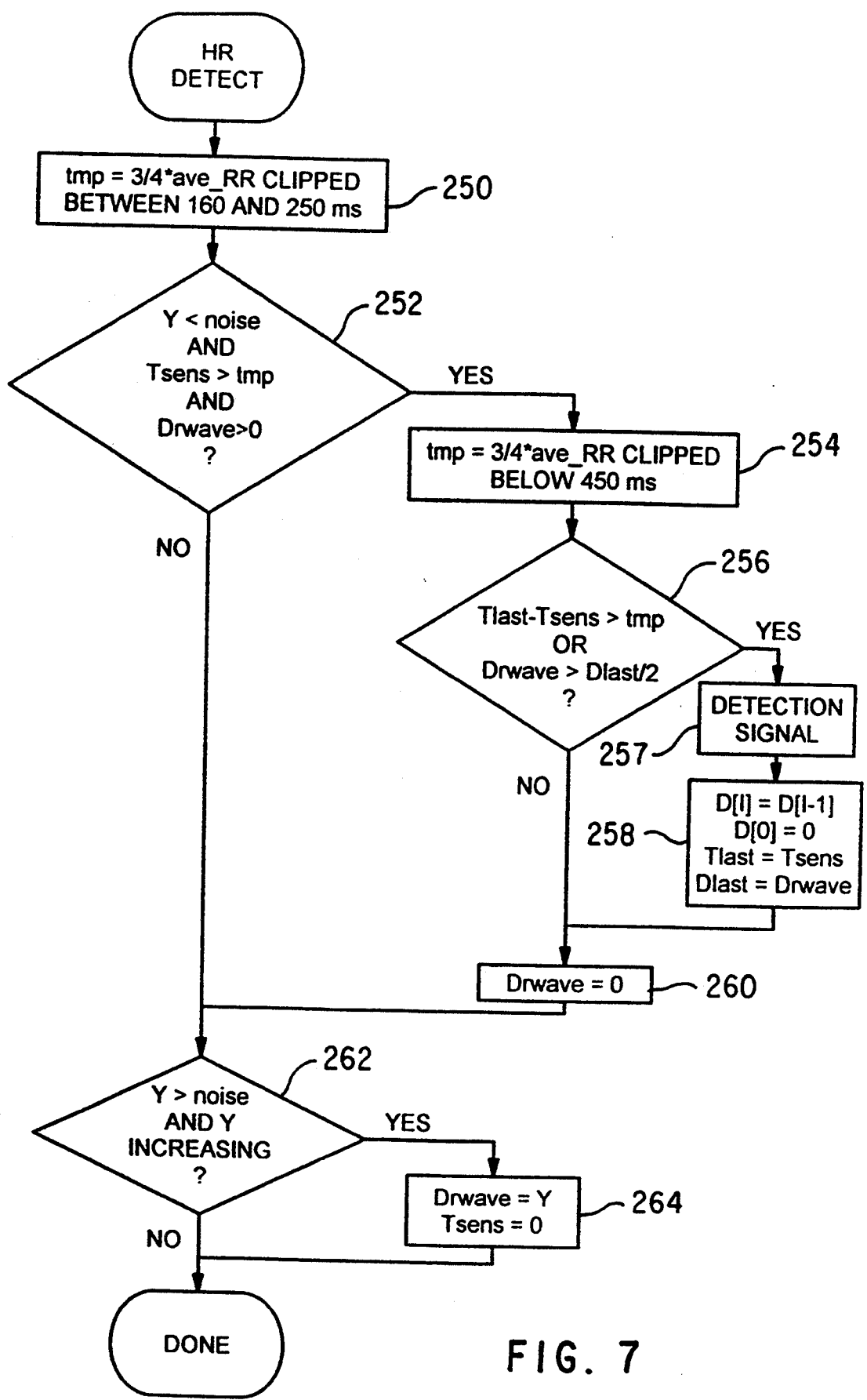
FIG. 7 shows a detailed flow diagram of the "HR Detect" step of the method shown in FIG. 4.

Refer to FIG. 7 where the algorithm used by the HR detector 162 is shown. Refer also to lines 171–193 of the sample program listing.

The HR detector 162 comprises two smaller routines. One routine detects a potential QRS complex and is shown in FIG. 7 by blocks 262 and 264 and in the sample program listing line 188–193. The other routine waits until the activity Y caused by the potential QRS complex has fallen beneath the noise threshold noise, which is at least a variable minimum time since the potential QRS complex occurred. The second routine is shown in FIG. 7 by blocks 250–260, and in the sample program listing lines 171–187.

Although the two routines of the HR detector 162 appear serially in FIG. 7 and in the sample program listing, they are mutually exclusive. That is, only one of the decision blocks 252 and 262 can be answered "yes" per execution of the HR detector routine. This can be seen most clearly by recognizing that decision block 252 which initiates one routine requires the activity Y to be less than the threshold noise while decision block 262 which initiates the other routine requires the activity Y to be greater than the threshold noise.

The HR detector 162 uses four storage registers. A first storage register Tlast contains the time that has elapsed since the occurrence of the last confirmed QRS complex that was detected by the HR detector. A second storage register named Dlast contains the peak magnitude of the activity Y of that last confirmed QRS complex. A third storage register is used to store the peak value of activity Y that represents a potential, yet unconfirmed, QRS complex. The fourth storage registers Tsens contain the time that has elapsed since the occurrence of that peak.

When the activity Y rises above both the noise detector output threshold noise and the peak activity Y that has been detected since the last confirmed QRS complex (that is, the peak amplitude that is stored in Drwave), then Drwave is set to the current activity Y and the Tsens timer is reset to zero 262,264. This effectively starts a variable timer of between 160 and 250 ms. Timer Tsens is updated 104 after each new value is read 102 from the ECG data stream X.

If the activity Y continues to increase with each new value in the ECG data stream, Drwave continues to be reset to the new higher activity and the Tsens timer continues to be reset to zero.

Once the activity Y starts to decrease, a QRS complex potentially has been detected. However, it cannot be assumed that the detected peak represents a QRS complex. First, the detected peak may have been caused by a P wave's activity Y rising above the noise threshold noise. Second, the activity Y caused by a valid QRS complex is not necessarily monotonically increasing. For example, a biphasic QRS waveform may cause an activity Y to have two pronounced humps. The higher of the two humps should signify the QRS complex. Third, the detected peak may have been caused by a T wave.

After the activity Y starts to decrease, the HR detector waits 252 between 160 and 250 ms (timed by timer Tsens) before attempting to determine if the detected peak is a QRS complex. If during this waiting period, an activity Y is detected that is higher than the peak, the peak is reset to the new value and the timer Tsens is reset to zero.

This variable time period is set long enough to allow a detected and normally conducted P wave to be overridden by the following QRS complex. It is also long enough to catch the higher of the two humps in activity caused by a biphasic QRS complex.

The time period is variable to adapt to faster or slower heart rates, and is set 250 to three-fourths the average R to R interval, clipped between 160 and 250 ms.

After passing the P wave discrimination 252, the potential detection must pass a second test before it is confirmed 256. This second test is designed to discriminate against T wave detection. Although T waves are generally wider, and thus do not cause as great an activity Y as the QRS complex, their activity can still exceed the threshold noise. Since a T wave can occur more than 250 ms after the QRS complex, they can pass the P wave discrimination decision block 252.

The T wave discriminator 254, 256 discriminates against T waves by requiring at least one of two conditions to be true before signaling detection 257: (1) the potential detection must occur 254 at least three-fourths the average R to R interval after the previously confirmed detection (capped at 450 ms), or (2) the amplitude Drwave of the potential detection must be at least half the amplitude Dlast of the previous confirmed detection.

An actual QRS complex will pass both tests, but a T wave will usually fail both. Because of its wider shape, the T wave causes a lower activity Y, preventing it from being at least half that of the last confirmed detection. Furthermore, a T wave will occur sooner than three-fourths the average R to R interval (capped at 450 ms) after the QRS complex.

Upon confirmation 256, the HR detector signals detection 257, and updates 258 its storage registers D[0], D[1], D[2], and D[3] which contain the peak absolute values of slope Z caused by the last four R waves. The HR detector also resets Tlast which contains the time since the last confirmed QRS complex detection to the time Tsens since the just confirmed detection. Drwave is set to Drwave, which is then reset to zero 260.

If the potential detection fails the T wave discrimination 254, the detected peak is discarded by resetting the peak detector Drwave to zero 260. Alternatively, the HR detector can reset Dlast to Drwave before resetting Drwave to zero and set Tlast to Tsens, even though the T wave discrimination failed.

As discussed above, the purpose of the sync detector 158 is to detect 116 the QRS complex with minimal time delay. The output from the sync detector can be used to initiate a synchronous discharge which must occur within 60 ms of the R wave peak.

As shown in FIG. 5, the sync detector 158 uses the slope Z from the slope detector 150, the LPF output threshold noise, and the maximum amplitudes D[1:3] of the activity Y for the last three confirmed QRS complex detections by the HR detector 162.

Figure 8:
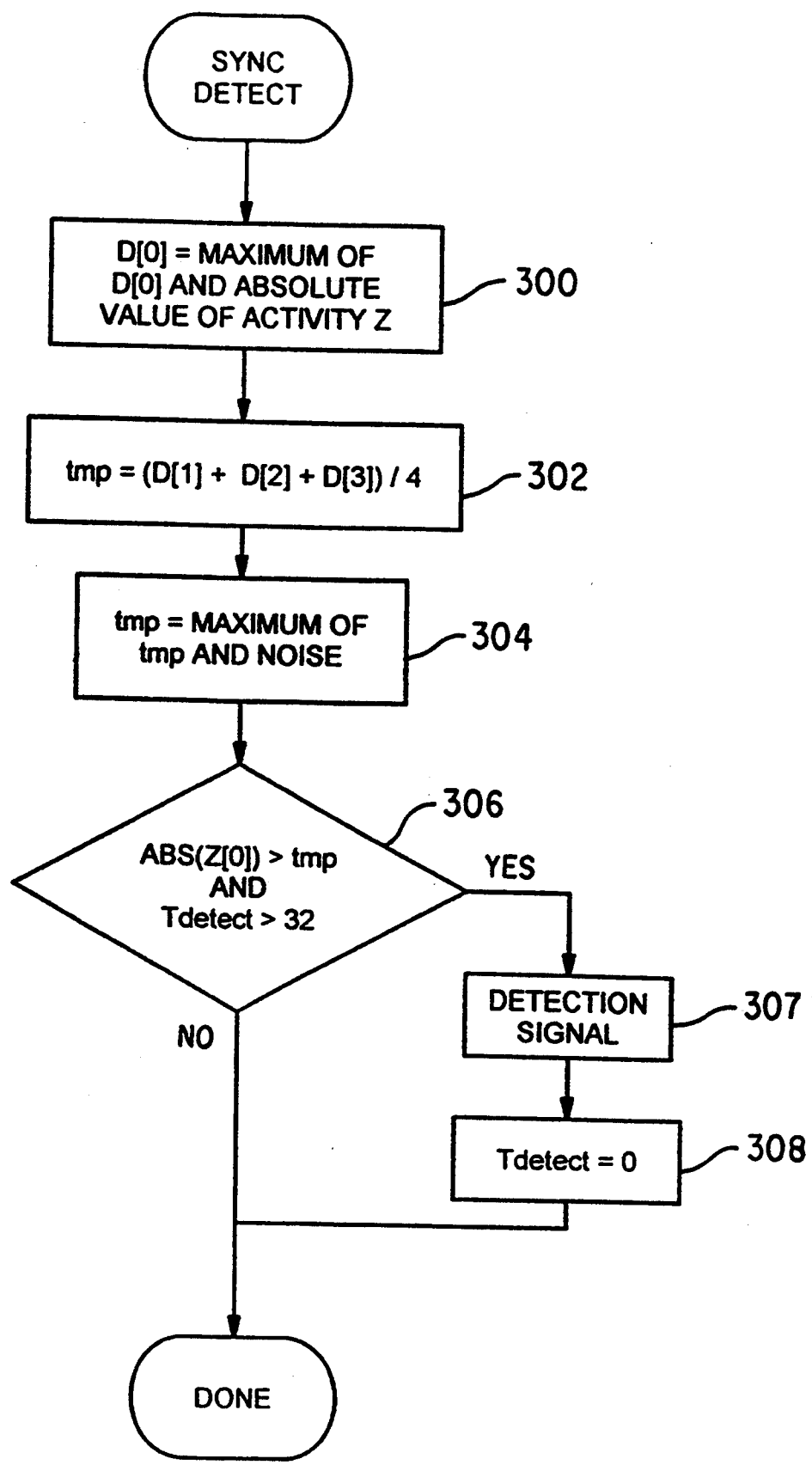
FIG. 8 shows a detailed flow diagram of the "Sync Detect" step of the method shown in FIG. 4.

Refer now to FIG. 8, where the algorithm used by the sync detector 158 is shown, and lines 203–212 of the sample program listing.

Two conditions must occur 306 for the sync detector 158 to detect a QRS complex. First, the absolute value of the slope Z must be greater than a threshold value named tmp and more than 175 ms must have elapsed since the last detection by the sync detector.

In block 300, storage register D[0] is assigned the greater of its current value or the absolute value of the slope Z. Since this assignment occurs for each new value in the ECG data stream X, and D[0] is reset to zero at each detection by the HR detector, D[0] represents the maximum absolute value of slope Z since the last QRS complex.

The threshold tmp is set 302 to three-fourths the average of D[1], D[2], and D[3]. If the LPF output noise is greater than the threshold tmp, tmp is set to noise. It is this threshold value of tmp which the absolute value of the slope Z must exceed to signify a QRS detection by the sync detector.

Upon detection, the timer Tdetect is reset to zero. This timer is updated 104 after each new value of ECG data is received.

Figure 6:
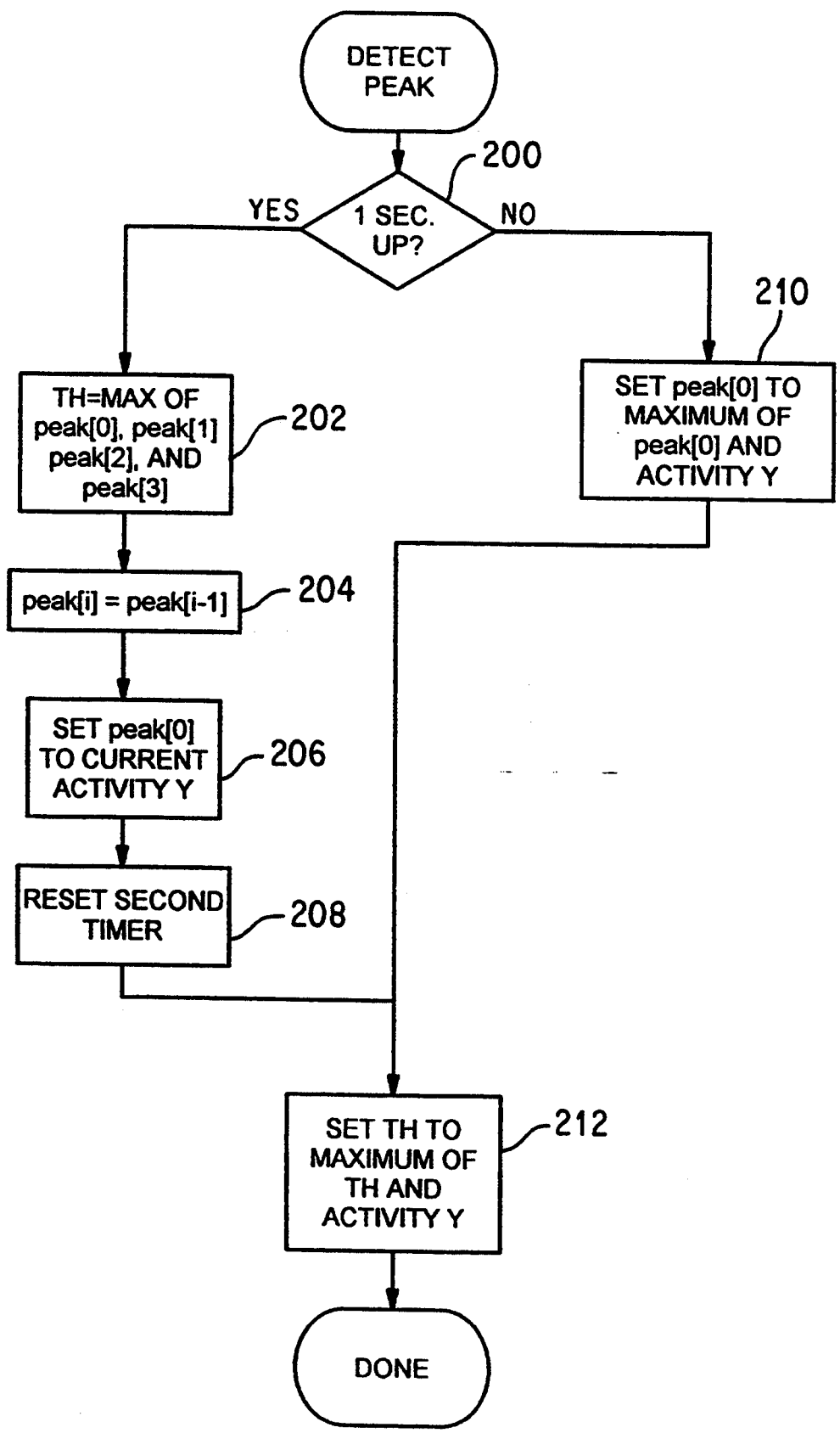
FIG. 6 shows a detailed flow diagram of the "Detect Peak" step of the method shown in FIG. 4.

Referring now to FIG. 6, the algorithm used by the peak detector 156 is shown. Three storage registers peak[1], peak[2], and peak[3] contain the maximum values of the activity Y for each of the four previous one-second time intervals, respectively. A current peak storage register peak[0] stores the maximum value of the activity Y for the current one-second interval. The threshold value TH output by the peak detector 156 is the maximum value of these four historical values and the current activity Y.

For each execution of the peak detection routine 112 by the peak detector 156, that is, once per each new value in the ECG data stream, a one-second timer is checked 200. If at least one second has passed since the timer was reset, the peak detector sets TH to the largest of the values contained in peak[1], peak[2], and peak[3]. The values contained in the storage registers are then shifted 204. That is, the value in peak[3] is discarded, the value in peak[2] is put in peak[3], the value in peak[1] is put in peak[2], and the value in peak[O] is put in peak[1]. The current peak storage register peak[0] is reset 206 to the current activity Y and the one second timer is reset 208. The threshold value TH is then set 212 to the larger of its current value TH and the current activity Y.

Alternatively, if one second has not passed since the one-second timer was reset, as determined in block 200, the current peak storage register peak[0] is set 210 to the larger of peak[0] and the current activity Y. The threshold value TH is then set 212 to the larger of TH and the current activity Y.

The peak detector 156 is implemented in lines 154–168 of the sample program listing.

The high-accuracy HR detector 160 uses an average time between R waves, that is, ave_RR, to vary a waiting period to skip over the P and T waves. Rather than use the output of the HR detector to determine the average time interval, an independent detector 160 is used to avoid a positive feedback situation.

As shown in FIG. 5, the independent detector 160 uses the threshold noise and the second threshold TH from the peak detector 156.

Figure 9:
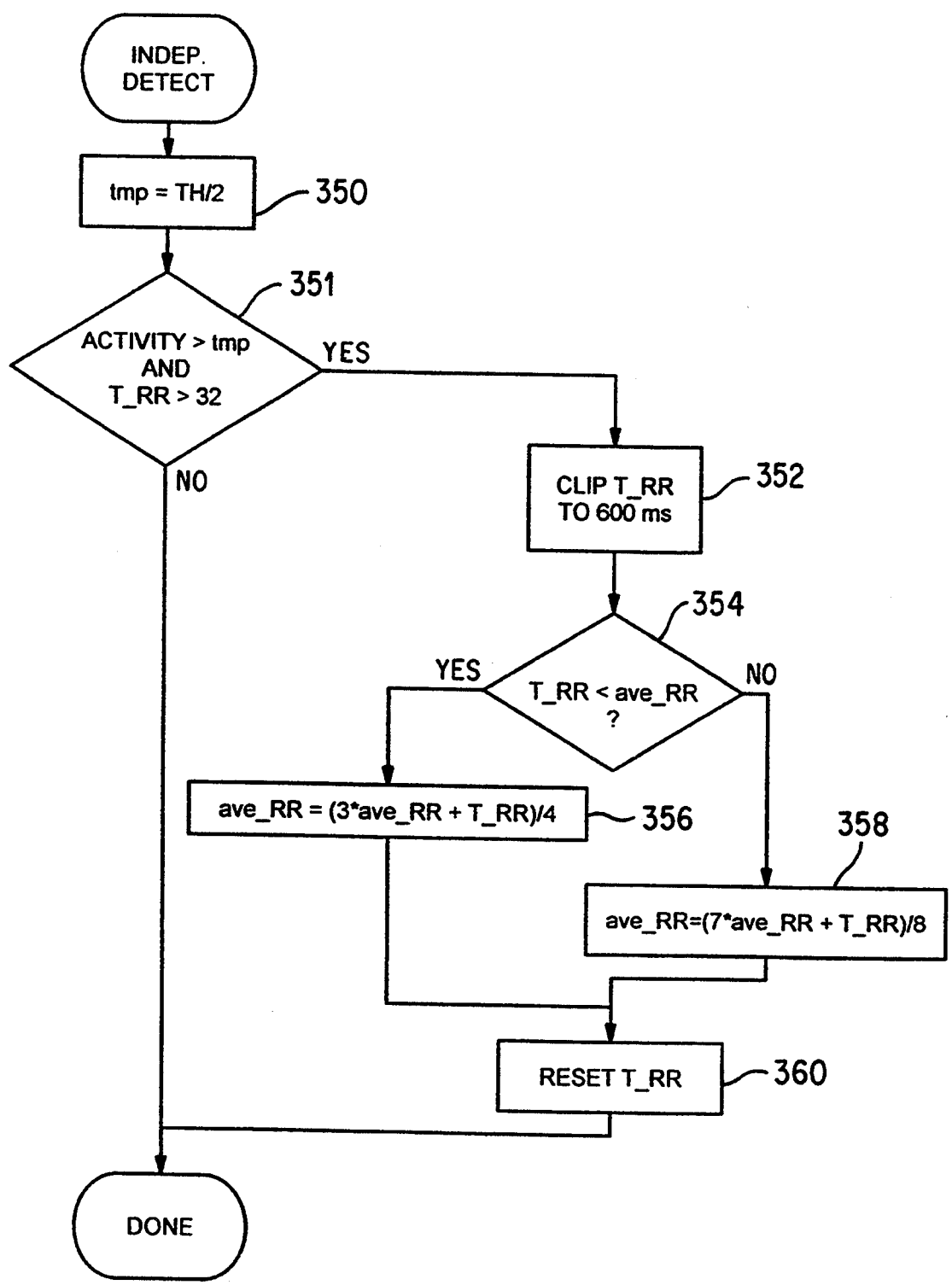
FIG. 9 shows a detailed flow diagram of the "Independent Detect" step of the method shown in FIG. 4.

Referring now to FIG. 9, the algorithm used by the independent detector 160 is shown. The second threshold TH from the peak detector 156 is divided in half. The time since the last independent detection is contained in the timer register T_RR which is updated 104 after each value is read from the ECG data stream X.

If 351 the current activity Y exceeds this resulting value and more than 160 ms has elapsed since the last detection by the independent detector, then a detection has occurred. In response, the independent detector 160 recalculates the average time between R waves ave RR. First, the value in T_RR is clipped 352 to 600 ms. If 354 the resulting T_RR is less than the current average time, then the new average time is calculated according to the following equation.

$$ave\_RR = (3 \cdot ave\_RR + T\_RR)/4 \qquad (2)$$

Otherwise, T_RR is calculated according to the following equation.

$$ave\_RR = (7 \cdot ave\_RR + T\_RR)/8 \qquad (3)$$

In this manner, the average time is allowed to decrease more rapidly than it increases.

Then the timer T_RR is reset 360 to zero.

Figure 10:
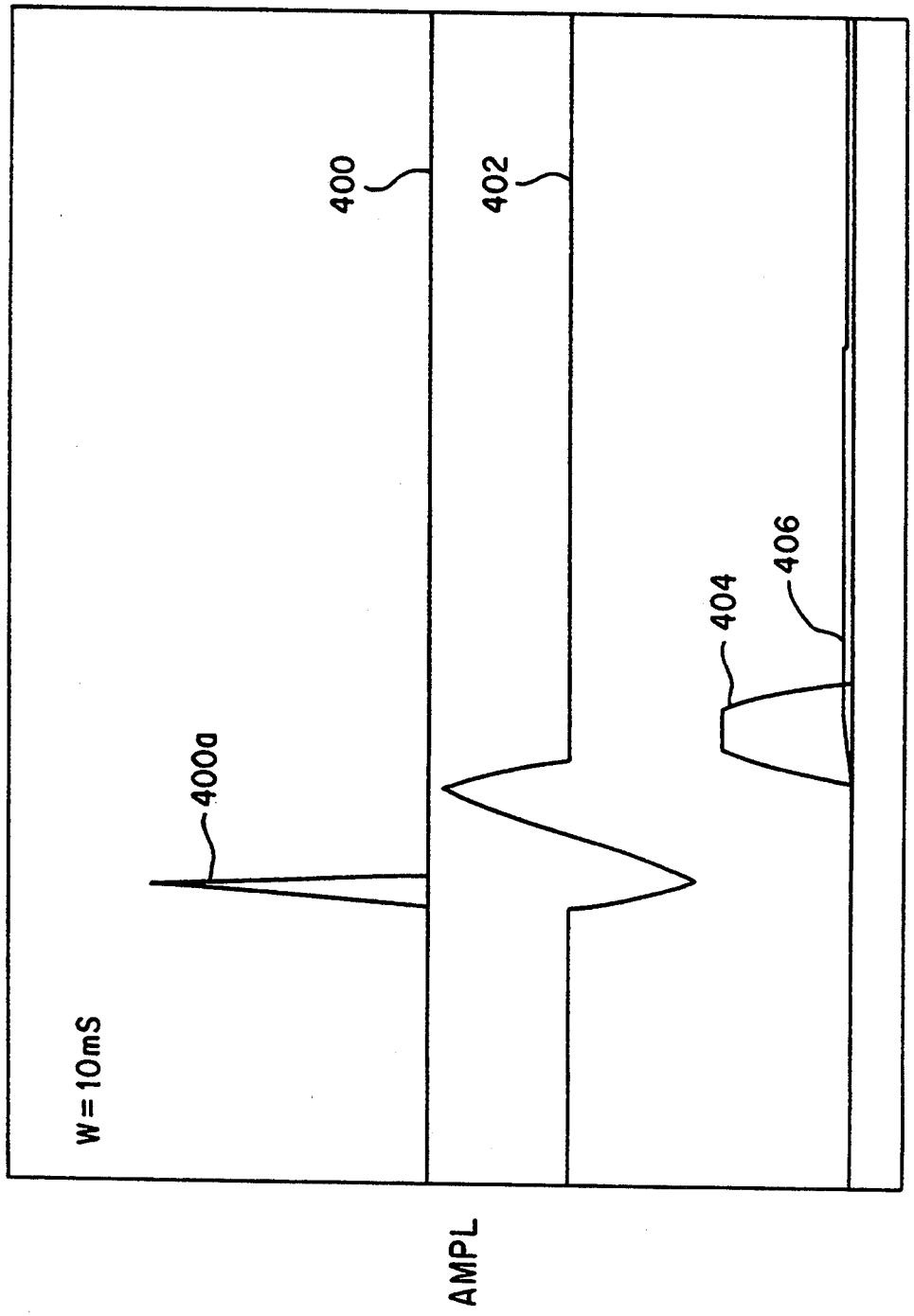
FIGS. 10 and 11 show the slope, activity and threshold values for two arbitrary input waveforms.
Figure 11:
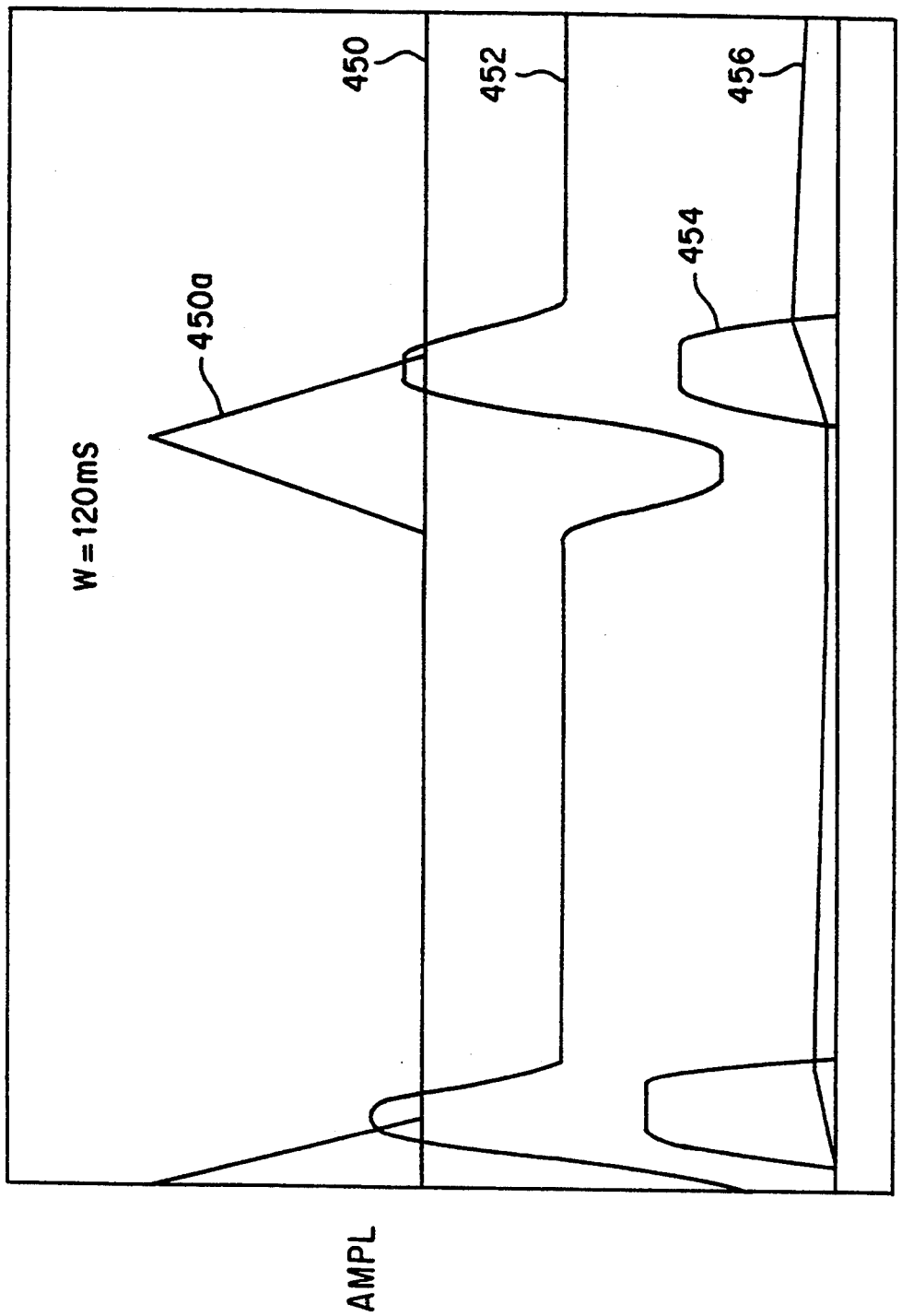

Referring now to FIGS. 10 and 11, four signals are shown. The top signal 400, 450 represents the input ECG data stream X with the triangular portion 400a, 450a representing a QRS complex. In FIG. 10, the triangular portion has a width of 10 ms, in FIG. 11, 120 ms. The second signal 402,452 represents the slope Z from the slope detector 150. The third signal 404, 454 represents the activity Y from the activity detector 152. The fourth signal 406, 456 represents the threshold noise.

Figure 12:
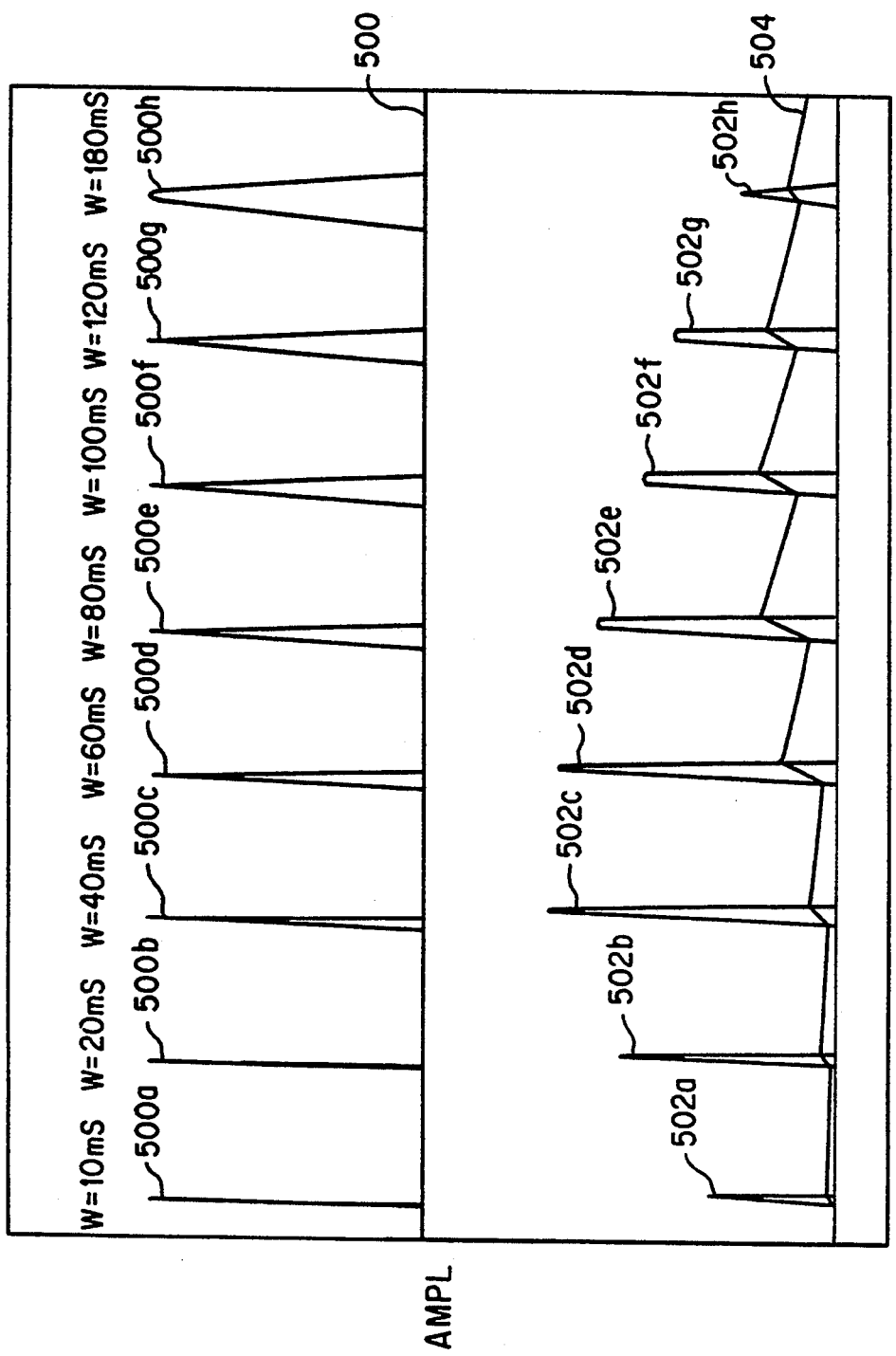
FIG. 12 shows the activity and threshold values for input triangular waveforms having various widths.
Figure 13:
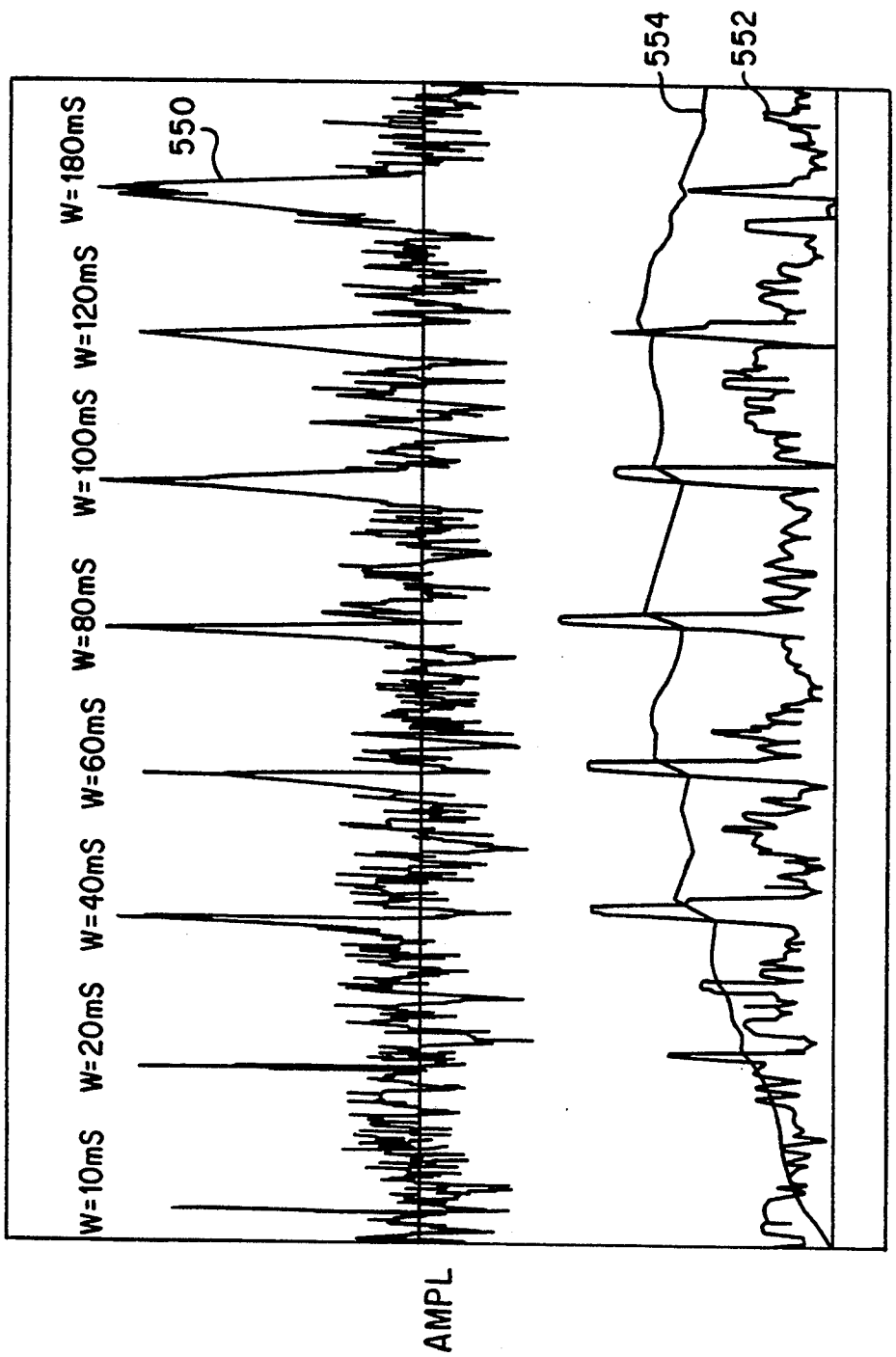
FIGS. 13 and 14 show activity and threshold values for input triangular waveforms having various widths superimposed on noise.
Figure 14:
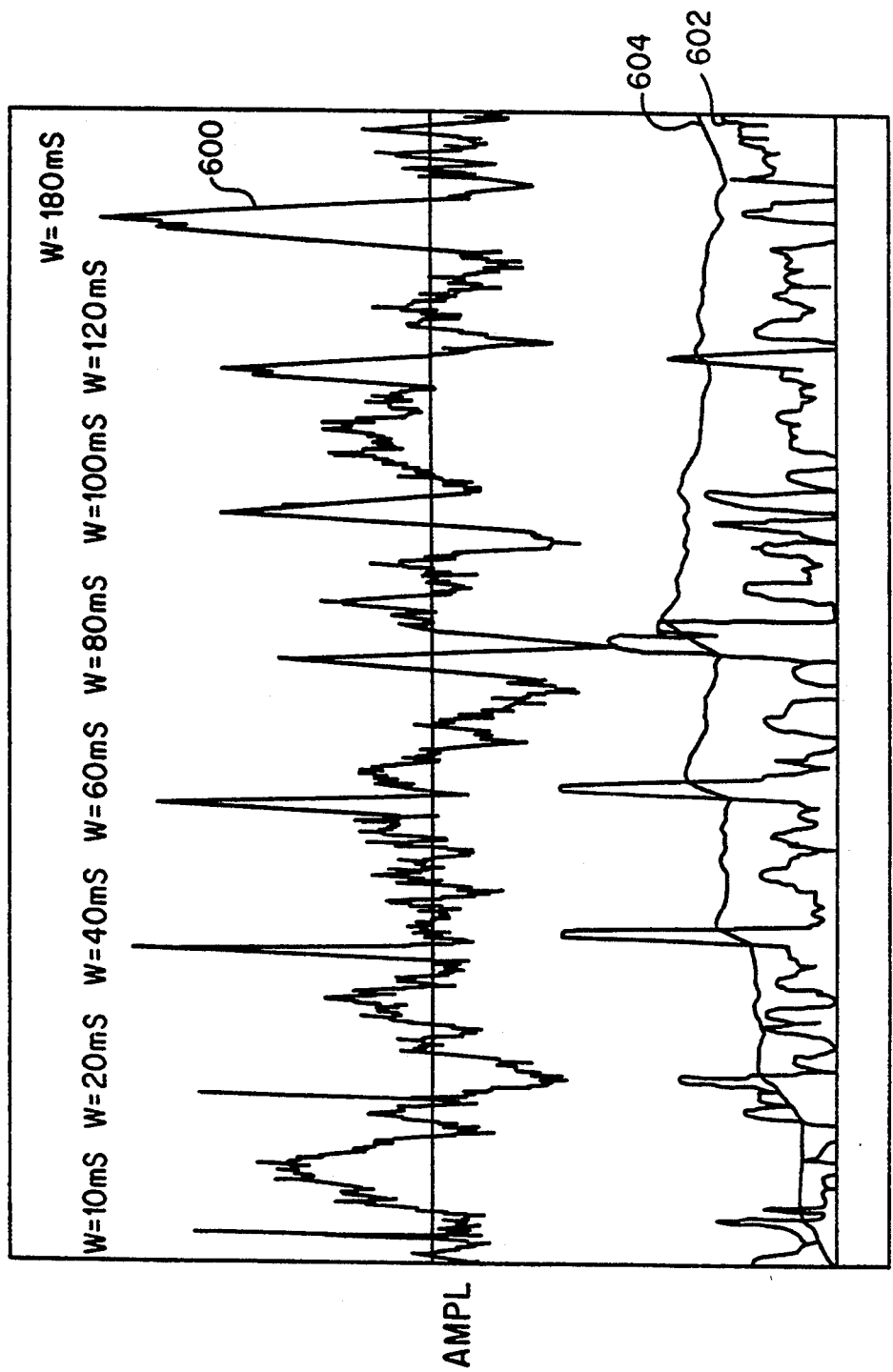

FIGS. 12–14 shows signals representing activity Y 502, 552, 602 and threshold noise 504, 554, 604 in response to an ECG data stream X 500, 550, 600 having triangular waveforms ranging from 10 ms to 180 ms in width. In FIG. 13, relatively high frequency noise is superimposed on the ECG data stream. In FIG. 14, "1/f" noise, which more closely approximates baseline wander conditions is superimposed on the ECG data stream.

Note that for both types of noise, the threshold noise quickly adjusts to a value which maximizes the detection of QRS complexes and minimizes the detection of noise.

Although the present invention has been described in considerable detail with reference to certain preferred versions and values, other versions are possible.

Although the method is described herein as being performed by a general purpose microprocessor on digitized data, this is not required. Hard-wired digital

What is claimed is:

1. A method for detecting QRS complexes in an ECG waveform, comprising the steps of:
   acquiring the ECG waveform;
   detecting activity from the ECG waveform;
   detecting a noise level from the ECG waveform;
   detecting a peak in activity when the activity is greater than the noise level;
   waiting a length of time shorter than an average R to R interval of the ECG waveform; and
   confirming said peak signifies a QRS complex if no other peaks having an amplitude greater than said noise level are detected during said length of time.

2. A method for detecting QRS complexes in an ECG waveform, comprising the steps of:
   acquiring the ECG waveform;
   detecting activity from the ECG waveform;
   detecting a noise level from the ECG waveform;
   detecting a peak in activity when the activity is greater than the noise level;
   waiting a length of time at least three fourths of an average R to R interval of the ECG waveform; and
   confirming said peak signifies a QRS complex if no other peaks having an amplitude greater than said noise level are detected during said length of time.

3. A method for detecting QRS complexes in an ECG waveform, comprising the steps of:
   acquiring the ECG waveform;
   detecting activity from the ECG waveform;
   detecting a noise level from the ECG waveform;
   detecting a peak in activity when the activity is greater than the noise level;
   waiting a length of tinge between 160 and 250 milliseconds; and
   confirming said peak signifies a QRS complex if no other peaks having an amplitude greater than said noise level are detected during said length of time.

4. A method for detecting QRS complexes in an ECG waveform, comprising the steps of:
   acquiring the ECG waveform;
   detecting activity from the ECG waveform;
   detecting a noise level from the ECG waveform;
   detecting a peak in activity when the activity is greater than the noise level;
   waiting a length of time shorter than an average R to R interval of the ECG waveform; and
   confirming said peak signifies a QRS complex if the amplitude of said peak is at least one half the amplitude of a previous peak, even if another peak greater than said noise level is detected during said length of time.

5. A QRS detector for detecting QRS complexes in an ECG waveform, comprising:
   means for acquiring the ECG waveform;
   means for detecting activity from the ECG waveform;
   means for detecting a noise level from the ECG waveform;
   means for detecting a peak in activity when the activity is greater than the noise level:
   means for waiting a length of time shorter than an average R to R interval of the ECG waveform; and
   means for confirming said peak signifies a QRS complex if no other peaks greater than said noise level are detected during said length of time.

* * * * *